(12) United States Patent
Kolich et al.

(10) Patent No.: US 9,771,003 B2
(45) Date of Patent: Sep. 26, 2017

(54) APPARATUS FOR CUSTOMIZING A VEHICLE SEAT FOR AN OCCUPANT

(71) Applicant: Ford Global Technologies, LLC, Dearborn, MI (US)

(72) Inventors: Michael Kolich, Windsor (CA); Amber LaVerne Hall, Oak Park, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 67 days.

(21) Appl. No.: 14/526,591

(22) Filed: Oct. 29, 2014

(65) Prior Publication Data

US 2016/0123793 A1 May 5, 2016

(51) Int. Cl.
| | | |
|---|---|---|
| *G06F 19/00* | (2011.01) | |
| *G05B 23/02* | (2006.01) | |
| *G01G 19/415* | (2006.01) | |
| *G01G 19/44* | (2006.01) | |
| *B60N 2/00* | (2006.01) | |
| *B60N 2/02* | (2006.01) | |
| *B60N 2/44* | (2006.01) | |

(Continued)

(52) U.S. Cl.
CPC ............ *B60N 2/02* (2013.01); *B60N 2/64* (2013.01); *G01G 19/4142* (2013.01); *A61B 5/6892* (2013.01); *B60N 2/0224* (2013.01); *B60N 2/0232* (2013.01); *B60N 2/4415* (2013.01); *B60N 2002/0268* (2013.01); *B60R 21/01516* (2014.10); *G01G 19/44* (2013.01)

(58) Field of Classification Search
CPC ............ A61B 5/0002; A61B 5/6893; B60R 21/01516; B60N 2/002; B60N 2/02; B60N 2/0244; B60N 2002/026; B60N 2002/0268; B60N 2/4415; B60N 2/0232; G01G 19/4142; G01G 19/44; G01G 19/12

See application file for complete search history.

(56) References Cited

U.S. PATENT DOCUMENTS 2,958,369 A  11/1960 Pitts et al.
3,403,938 A  10/1968 Cramer et al.
(Continued)

FOREIGN PATENT DOCUMENTS

EP  0754590  1/1997
EP  0926969  1/2002
(Continued)

OTHER PUBLICATIONS

M. Grujicic et al., "Seat-cushion and soft-tissue material modeling and a finite element investigation of the seating comfort for passenger-vehicle occupants," Materials and Design 30 (2009) 4273-4285.

(Continued)

*Primary Examiner* — Randy Gibson
(74) *Attorney, Agent, or Firm* — Vichit Chea; Price Heneveld LLP (57) ABSTRACT

An apparatus for customizing a vehicle seat includes a seat having a cushion and a back coupled thereto and a plurality of force sensors in respective locations along the cushion and the back. The apparatus further includes electronic circuitry coupled with the plurality of sensors and programmed to associate forces sensed by ones of the plurality of force sensors with the respective locations thereof and to output the sensed forces and associated areas.

18 Claims, 6 Drawing Sheets

(51) Int. Cl.
*G01L 5/00* (2006.01)
*B60N 2/64* (2006.01)
*G01G 19/414* (2006.01)
*A61B 5/00* (2006.01)
*B60R 21/015* (2006.01)

(56) References Cited

U.S. PATENT DOCUMENTS

| | | |
|---|---|---|
| 3,929,374 A | 12/1975 | Hogan et al. |
| 4,324,431 A | 4/1982 | Murphy et al. |
| 4,334,709 A | 6/1982 | Akiyama et al. |
| 4,353,595 A | 10/1982 | Kaneko et al. |
| 4,541,669 A | 9/1985 | Goldner |
| 4,629,248 A | 12/1986 | Mawbey |
| 4,720,141 A | 1/1988 | Sakamoto et al. |
| 4,890,235 A * | 12/1989 | Reger .............. A47C 31/126 264/222 |
| 4,915,447 A | 4/1990 | Shovar |
| 5,060,174 A * | 10/1991 | Gross .............. A47C 31/126 702/139 |
| 5,171,062 A | 12/1992 | Courtois |
| 5,174,526 A | 12/1992 | Kanigowski |
| 5,518,294 A | 5/1996 | Ligon, Sr. et al. |
| 5,560,681 A | 10/1996 | Dixon et al. |
| 5,642,302 A * | 6/1997 | Dumont .............. B60N 2/0232 128/845 |
| 5,647,635 A | 7/1997 | Aumond et al. |
| 5,755,493 A | 5/1998 | Kodaverdian |
| 5,769,489 A | 6/1998 | Dellanno |
| 5,826,938 A | 10/1998 | Yanase et al. |
| 5,836,648 A | 11/1998 | Karschin et al. |
| 5,902,014 A | 5/1999 | Dinkel et al. |
| 5,913,568 A | 6/1999 | Brightbill et al. |
| 5,930,152 A * | 7/1999 | Dumont .............. B60N 2/0224 128/845 |
| 5,951,039 A | 9/1999 | Severinski et al. |
| 5,975,629 A | 11/1999 | Lorbiecki |
| 6,024,406 A | 2/2000 | Charras et al. |
| 6,062,642 A | 5/2000 | Sinnhuber et al. |
| 6,145,925 A | 11/2000 | Eksin et al. |
| 6,155,593 A | 12/2000 | Kimura et al. |
| 6,179,379 B1 | 1/2001 | Andersson |
| 6,189,966 B1 | 2/2001 | Faust et al. |
| 6,196,627 B1 | 3/2001 | Faust et al. |
| 6,206,466 B1 | 3/2001 | Komatsu |
| 6,217,062 B1 | 4/2001 | Breyvogel et al. |
| 6,220,661 B1 | 4/2001 | Peterson |
| 6,224,150 B1 | 5/2001 | Eksin et al. |
| 6,296,308 B1 | 10/2001 | Cosentino et al. |
| 6,312,050 B1 | 11/2001 | Eklind |
| 6,320,510 B2 * | 11/2001 | Menkedick .............. 340/5.1 |
| 6,345,839 B1 * | 2/2002 | Kuboki .............. B60R 21/01516 280/735 |
| 6,364,414 B1 | 4/2002 | Specht |
| 6,375,269 B1 | 4/2002 | Maeda et al. |
| 6,394,546 B1 | 5/2002 | Knoblock et al. |
| 6,403,897 B1 * | 6/2002 | Bluth .............. A61B 5/0002 128/920 |
| 6,428,124 B1 * | 8/2002 | Bluth .............. A61B 5/0002 177/245 |
| 6,454,353 B1 | 9/2002 | Knaus |
| 6,523,892 B1 | 2/2003 | Kage et al. |
| 6,550,856 B1 | 4/2003 | Ganser et al. |
| 6,565,150 B2 | 5/2003 | Fischer et al. |
| 6,619,605 B2 | 9/2003 | Lambert |
| 6,649,848 B2 * | 11/2003 | Kriger .............. G01G 19/4146 128/921 |
| 6,682,140 B2 | 1/2004 | Minuth et al. |
| 6,695,406 B2 | 2/2004 | Plant |
| 6,698,832 B2 | 3/2004 | Boudinot |
| 6,736,452 B2 | 5/2004 | Aoki et al. |
| 6,758,522 B2 | 7/2004 | Ligon, Sr. et al. |
| 6,808,230 B2 | 10/2004 | Buss et al. |
| 6,820,930 B2 | 11/2004 | Dellanno |
| 6,824,212 B2 | 11/2004 | Malsch et al. |
| 6,848,742 B1 | 2/2005 | Aoki et al. |
| 6,860,559 B2 | 3/2005 | Schuster, Sr. et al. |
| 6,860,564 B2 | 3/2005 | Reed et al. |
| 6,866,339 B2 | 3/2005 | Itoh |
| 6,869,140 B2 | 3/2005 | White et al. |
| 6,890,029 B2 | 5/2005 | Svantesson |
| 6,938,953 B2 | 9/2005 | Håland et al. |
| 6,955,399 B2 | 10/2005 | Hong |
| 6,962,392 B2 | 11/2005 | O'Connor |
| 6,988,770 B2 | 1/2006 | Witchie |
| 6,997,473 B2 | 2/2006 | Tanase et al. |
| 7,040,699 B2 | 5/2006 | Curran et al. |
| 7,100,992 B2 | 9/2006 | Bargheer et al. |
| 7,131,694 B1 | 11/2006 | Buffa |
| 7,159,934 B2 | 1/2007 | Farquhar et al. |
| 7,185,950 B2 | 3/2007 | Pettersson et al. |
| 7,213,876 B2 | 5/2007 | Stoewe |
| 7,229,118 B2 | 6/2007 | Saberan et al. |
| 7,248,996 B2 * | 7/2007 | Uenishi .............. A61B 5/18 702/173 |
| 7,261,371 B2 | 8/2007 | Thunissen et al. |
| 7,344,189 B2 | 3/2008 | Reed et al. |
| 7,350,859 B2 | 4/2008 | Klukowski |
| 7,393,005 B2 | 7/2008 | Inazu et al. |
| 7,425,034 B2 | 9/2008 | Bajic et al. |
| 7,441,838 B2 | 10/2008 | Patwardhan |
| 7,465,272 B2 * | 12/2008 | Kriger .............. G01G 19/4146 128/921 |
| 7,467,823 B2 | 12/2008 | Hartwich |
| 7,478,869 B2 | 1/2009 | Lazanja et al. |
| 7,481,489 B2 | 1/2009 | Demick |
| 7,506,924 B2 | 3/2009 | Bargheer et al. |
| 7,506,938 B2 | 3/2009 | Brennan et al. |
| 7,530,633 B2 | 5/2009 | Yokota et al. |
| 7,543,888 B2 | 6/2009 | Kuno |
| 7,578,552 B2 | 8/2009 | Bajic et al. |
| 7,597,398 B2 | 10/2009 | Lindsay |
| 7,609,168 B2 * | 10/2009 | Boverie .............. A61B 5/11 180/273 |
| 7,614,693 B2 | 11/2009 | Ito |
| 7,641,281 B2 | 1/2010 | Grimm |
| 7,669,925 B2 | 3/2010 | Beck et al. |
| 7,669,928 B2 | 3/2010 | Snyder |
| 7,712,833 B2 | 5/2010 | Ueda |
| 7,717,459 B2 | 5/2010 | Bostrom et al. |
| 7,726,733 B2 | 6/2010 | Balser et al. |
| 7,735,932 B2 | 6/2010 | Lazanja et al. |
| 7,752,720 B2 | 7/2010 | Smith |
| 7,753,451 B2 | 7/2010 | Maebert et al. |
| 7,775,602 B2 | 8/2010 | Lazanja et al. |
| 7,784,863 B2 | 8/2010 | Fallen |
| 7,802,843 B2 | 9/2010 | Andersson et al. |
| 7,819,470 B2 | 10/2010 | Humer et al. |
| 7,823,971 B2 | 11/2010 | Humer et al. |
| 7,845,729 B2 | 12/2010 | Yamada et al. |
| 7,857,381 B2 | 12/2010 | Humer et al. |
| 7,871,126 B2 | 1/2011 | Becker et al. |
| 7,891,701 B2 | 2/2011 | Tracht et al. |
| 7,909,360 B2 | 3/2011 | Marriott et al. |
| 7,931,294 B2 | 4/2011 | Okada et al. |
| 7,931,330 B2 | 4/2011 | Itou et al. |
| 7,946,649 B2 | 5/2011 | Galbreath et al. |
| 7,963,553 B2 | 6/2011 | Huynh et al. |
| 7,963,595 B2 | 6/2011 | Ito et al. |
| 7,963,600 B2 | 6/2011 | Alexander et al. |
| 7,971,931 B2 | 7/2011 | Lazanja et al. |
| 7,971,937 B2 | 7/2011 | Ishii et al. |
| 8,011,726 B2 | 9/2011 | Omori et al. |
| 8,016,355 B2 | 9/2011 | Ito et al. |
| 8,029,055 B2 | 10/2011 | Hartlaub |
| 8,038,222 B2 | 10/2011 | Lein et al. |
| 8,075,053 B2 | 12/2011 | Tracht et al. |
| 8,109,569 B2 | 2/2012 | Mitchell |
| 8,123,246 B2 | 2/2012 | Gilbert et al. |
| 8,128,167 B2 | 3/2012 | Zhong et al. |
| 8,162,391 B2 | 4/2012 | Lazanja et al. |
| 8,162,397 B2 | 4/2012 | Booth et al. |
| 8,167,370 B2 | 5/2012 | Arakawa et al. |

(56) References Cited

U.S. PATENT DOCUMENTS

| | | | |
|---|---|---|---|
| 8,210,568 B2 | 7/2012 | Ryden et al. | |
| 8,210,605 B2 | 7/2012 | Hough et al. | |
| 8,210,611 B2 | 7/2012 | Aldrich et al. | |
| 8,226,165 B2 | 7/2012 | Mizoi | |
| 8,342,607 B2 | 1/2013 | Hofmann et al. | |
| 8,616,654 B2* | 12/2013 | Zenk | B60N 2/0244 297/284.3 |
| 8,698,014 B1* | 4/2014 | Walstad | G01G 19/44 177/126 |
| 9,103,747 B2* | 8/2015 | Galbreath | A61B 5/1036 |
| 2002/0167486 A1* | 11/2002 | Tan | B60N 2/002 345/156 |
| 2004/0195870 A1 | 10/2004 | Bohlender et al. | |
| 2005/0200166 A1 | 9/2005 | Noh | |
| 2006/0043777 A1 | 3/2006 | Friedman et al. | |
| 2007/0120401 A1 | 5/2007 | Minuth et al. | |
| 2007/0146131 A1* | 6/2007 | Boverie | A61B 5/11 340/540 |
| 2007/0296600 A1* | 12/2007 | Dixon | A61G 7/05 340/573.1 |
| 2008/0036252 A1* | 2/2008 | Breed | B60J 10/00 297/217.2 |
| 2008/0174159 A1 | 7/2008 | Kojima et al. | |
| 2009/0066122 A1 | 3/2009 | Minuth et al. | |
| 2009/0165263 A1 | 7/2009 | Smith | |
| 2009/0322124 A1 | 12/2009 | Barkow et al. | |
| 2010/0038937 A1 | 2/2010 | Andersson et al. | |
| 2010/0140986 A1 | 6/2010 | Sawada | |
| 2010/0171346 A1 | 7/2010 | Laframboise et al. | |
| 2010/0187881 A1 | 7/2010 | Fujita et al. | |
| 2010/0201167 A1 | 8/2010 | Wieclawski | |
| 2010/0231013 A1 | 9/2010 | Schlenker | |
| 2010/0270840 A1 | 10/2010 | Tanaka et al. | |
| 2010/0301650 A1 | 12/2010 | Hong | |
| 2010/0320816 A1 | 12/2010 | Michalak | |
| 2011/0018498 A1 | 1/2011 | Soar | |
| 2011/0074185 A1 | 3/2011 | Nakaya et al. | |
| 2011/0095513 A1 | 4/2011 | Tracht et al. | |
| 2011/0095578 A1 | 4/2011 | Festag | |
| 2011/0109127 A1 | 5/2011 | Park et al. | |
| 2011/0109128 A1 | 5/2011 | Axakov et al. | |
| 2011/0121624 A1 | 5/2011 | Brncick et al. | |
| 2011/0133525 A1 | 6/2011 | Oota | |
| 2011/0163574 A1 | 7/2011 | Tame et al. | |
| 2011/0163583 A1 | 7/2011 | Zhong et al. | |
| 2011/0186560 A1 | 8/2011 | Kennedy et al. | |
| 2011/0187174 A1 | 8/2011 | Tscherbner | |
| 2011/0254335 A1 | 10/2011 | Pradier et al. | |
| 2011/0260506 A1 | 10/2011 | Kuno | |
| 2011/0272548 A1 | 11/2011 | Rudkowski et al. | |
| 2011/0272978 A1 | 11/2011 | Nitsuma | |
| 2011/0278885 A1 | 11/2011 | Procter et al. | |
| 2011/0278886 A1 | 11/2011 | Nitsuma | |
| 2011/0298261 A1 | 12/2011 | Holt et al. | |
| 2012/0032486 A1 | 2/2012 | Baker et al. | |
| 2012/0037754 A1 | 2/2012 | Kladde | |
| 2012/0063081 A1 | 3/2012 | Grunwald | |
| 2012/0080914 A1 | 4/2012 | Wang | |
| 2012/0086249 A1* | 4/2012 | Hotary | B60N 2/0228 297/284.3 |
| 2012/0091695 A1 | 4/2012 | Richez et al. | |
| 2012/0091766 A1 | 4/2012 | Yamaki et al. | |
| 2012/0091779 A1 | 4/2012 | Chang et al. | |
| 2012/0096960 A1* | 4/2012 | Galbreath | A61B 5/1036 73/866.4 |
| 2012/0109468 A1 | 5/2012 | Baumann et al. | |
| 2012/0119551 A1 | 5/2012 | Brncick et al. | |
| 2012/0125959 A1 | 5/2012 | Kucera | |
| 2012/0127643 A1 | 5/2012 | Mitchell | |
| 2012/0129440 A1 | 5/2012 | Kitaguchi et al. | |
| 2012/0162891 A1 | 6/2012 | Tranchina et al. | |
| 2012/0175924 A1 | 7/2012 | Festag et al. | |
| 2012/0187729 A1 | 7/2012 | Fukawatase et al. | |
| 2012/0248833 A1 | 10/2012 | Hontz et al. | |
| 2012/0261974 A1 | 10/2012 | Yoshizawa et al. | |
| 2013/0076092 A1 | 3/2013 | Kulkarni et al. | |
| 2013/0332104 A1* | 12/2013 | Russell | A61B 5/1036 702/139 |
| 2014/0032043 A1 | 1/2014 | Line et al. | |
| 2015/0008710 A1* | 1/2015 | Young | B60N 2/0276 297/217.3 |
| 2015/0351692 A1* | 12/2015 | Pereny | A61B 5/486 297/217.3 |
| 2015/0352990 A1* | 12/2015 | Zouzal | B60N 2/665 297/284.3 |
| 2015/0366350 A1* | 12/2015 | Di Censo | A47C 1/00 700/275 |

FOREIGN PATENT DOCUMENTS

| | | |
|---|---|---|
| EP | 1266794 | 3/2004 |
| EP | 1123834 | 10/2004 |
| EP | 1050429 | 10/2005 |
| EP | 1084901 | 6/2006 |
| EP | 1674333 | 8/2007 |
| EP | 1950085 | 12/2008 |
| EP | 1329356 | 11/2009 |
| JP | 201178557 A | 4/2011 |
| WO | WO9511818 | 5/1995 |
| WO | WO9958022 | 11/1999 |
| WO | WO2006131189 | 12/2006 |
| WO | WO2007028015 | 8/2007 |
| WO | 2008019981 A1 | 2/2008 |
| WO | WO2008073285 | 6/2008 |
| WO | WO2011021952 | 2/2011 |
| WO | 2011068684 A1 | 6/2011 |
| WO | WO2012008904 | 1/2012 |

OTHER PUBLICATIONS

"Thigh Support for Tall Drivers," http://cars.about.com/od/infiniti/ig/2009-Infiniti-G37-Coupe-pics/2008-G37-cpe-thigh-support.htm (1 page).

Mladenov, "Opel Insignia Receives Seal of Approval for Ergonomic Seats," Published Aug. 27, 2008, http://www.automobilesreview.com/auto-news/opel-insignia-receives-seal-of-approval-for-ergonomic-seats/4169/ (2 pages).

Brose India Automotive Systems, "Adaptive Sensor Controlled Headrest," http://www.indiamart.com/broseindiaautomotive-systems/products.html, Oct. 9, 2012 (12 pages).

eCOUSTICS.COM, "Cineak Motorized Articulating Headrest Preview," http://www.ecoustics.com/ah/reviews/furniture/accessories/cineak-motorized-headrest, Oct. 9, 2012 (3 pages).

"Performance' Car Seat Eliminates Steel," Published in Plastics News—Indian Edition Plastics & Polymer News, (http://www.plasticsinfomart.com/performance-car-seat-eliminates-steel/), Jan. 2012, 3 pages.

"Frankfurt 2009 Trend —Light and Layered." by Hannah Macmurray, Published in GreenCarDesign, (http://www.greencardesign.com/site/trends/00138-frankfurt-2009-trend-light-and-layered), Sep. 2009, 9 pages.

"Imola Pro-fit", Cobra, (http://cobra.subesports.com/products/cat/seats/brand/Cobra/prodID/656), Date unknown, 2 pages.

* cited by examiner

APPARATUS FOR CUSTOMIZING A VEHICLE SEAT FOR AN OCCUPANT

FIELD OF THE INVENTION

The present invention generally relates to a method and related apparatus for customizing a vehicle seat. More particularly, the apparatus includes a kiosk capable of implementing the method to determine a custom seat configuration for a vehicle seat.

BACKGROUND OF THE INVENTION

Motor vehicle seats, particularly driver seats and front passenger seats may include a number of moveable parts for cooperatively supporting various portions of an occupant. Relative movement of the seat parts may provide for numerous modes of customizing the seating surface that the seat parts define to suit a particular user. Further, many seats include mechanisms for automated or motorized movement of the seat parts as well as memory to store a particular seat configuration for automated movement of the seat parts into that particular configurations.

It may, accordingly, be advantageous to provide an apparatus and method to identify a comfortable seat configuration for a particular potential occupant of such a customizable vehicle seat such that the seat configuration can be implemented in a vehicle seat associated with the potential occupant.

SUMMARY OF THE INVENTION

According to one aspect of the present invention, an apparatus for customizing a vehicle seat includes a seat having a cushion and a back coupled thereto and a plurality of force sensors in respective locations along the cushion and the back. The apparatus further includes electronic circuitry coupled with the plurality of sensors and programmed to associate forces sensed by ones of the plurality of force sensors with the respective locations thereof and to output the sensed forces and associated areas.

According to another aspect of the present invention, a method for customizing a vehicle seat includes obtaining data related to a weight distribution of an occupant over a test seat in a test configuration and including a cushion, a back, and a plurality of force sensors distributed along the cushion and the back, the data being obtained using the sensors. The method further includes determining a custom configuration for a vehicle seat based on the weight distribution data of the occupant.

According to another aspect of the present invention, a kiosk for determining a custom vehicle seat configuration includes a test seat having a plurality of force sensors distributed adjacent a seating surface thereof and electronic circuitry coupled with the plurality of sensors. The kiosk further includes a control coupled with the electronic circuitry and operable to instruct the electronic circuitry to obtain force measurements from the sensors and a display coupled with the electronic circuitry. The electronic circuitry is operable to output information related to the force measurements on the display.

The various aspects of the present invention can provide a customized seat arrangement for a particular passenger in a vehicle seat. In an example, the customized seat arrangement can be easily implemented in a vehicle that the test subject, or occupant, intends to use.

These and other aspects, objects, and features of the present invention will be understood and appreciated by those skilled in the art upon studying the following specification, claims, and appended drawings.

DETAILED DESCRIPTION OF THE PREFERRED EMBODIMENTS

Figure 1:
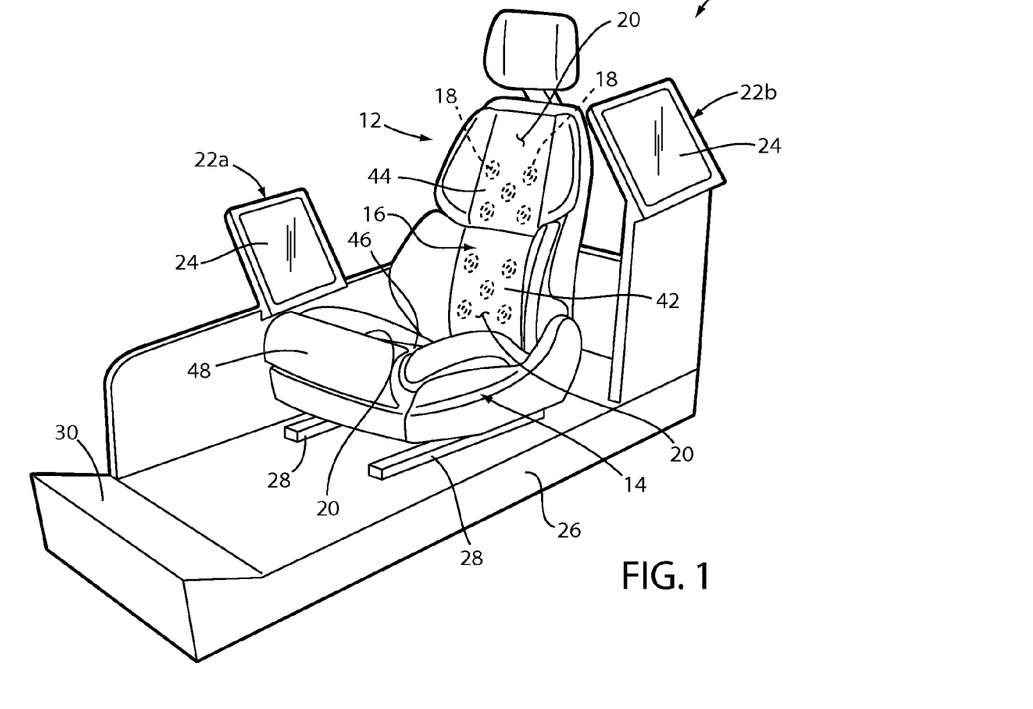
FIG. 1 is a front perspective view of a kiosk for determining a custom vehicle seat configuration.

For purposes of description herein, the terms "upper," "lower," "right," "left," "rear," "front," "vertical," "horizontal," "interior," "exterior," and derivatives thereof shall relate to the invention as oriented in FIG. 1. However, it is to be understood that the invention may assume various alternative orientations, except where expressly specified to the contrary. It is also to be understood that the specific devices and processes illustrated in the attached drawing, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise. Additionally, unless otherwise specified, it is to be understood that discussion of a particular feature of component extending in or along a given direction or the like does not mean that the feature or component follows a straight line or axis in such a direction or that it only extends in such direction or on such a plane without other directional components or deviations, unless otherwise specified.

Referring to FIG. 1, reference numeral 10 generally designates an apparatus generally depicted in the form of a kiosk for customizing a vehicle seat. Kiosk 10 includes a seat 12 having a cushion 14 and a back 16 coupled with the cushion 14. A plurality of force sensors 18 are distributed along the cushion 14 and back 16. Kiosk 10 further includes electronic circuitry internal thereto (not shown in FIG. 1) coupled with the plurality of sensors 18 and programmed to associate forces sensed by respective ones of the plurality of force sensors 18 with the particular locations thereof along cushion 14 and back 16 and to output the sensed forces and associated areas.

As described further below, the seat included in kiosk 10 can be in the form of a test seat 12 that is generally designed to mimic the shape and configuration of a vehicle seat (such as vehicle seat 112 in FIG. 7), including the general contours of seating surface 20 and the general adjustment modes, including movement between and among various parts thereof. In an example, test seat 12 can be a modified vehicle seat of the type intended to be customized using kiosk 10 (as described below). Kiosk 10 can use measurement data obtained from force sensors 18 to determine a configuration for vehicle seat 112 (FIG. 7) that may provide increased comfort for an occupant by distributing the weight of the occupant across seating surface 20 as evenly as possible and with particular attention to minimizing the occurrence of pressure points. As shown in FIG. 1, test seat 12 can be a modified version of an actual vehicle seat, with modifications thereto including the installation of sensors 18 and the addition of any wiring associated therewith. Kiosk 10 can further include one or more control units 22a and 22b for an occupant of test seat 12 (such as by control 22a) or a designated operator of kiosk 10 (using control unit 22b) to direct kiosk 10 to take force measurements of test seat 12 with an occupant therein, as well as to control various output protocols of kiosk 10, as described further below. Variations of kiosk 10 can include only one of control units 22a and 22b, or additional control units as needed. As illustrated, control units 22a and 22b can include displays 24 which may be in the form of video displays with or without touch screen functionality, allowing control units 22a and 22b to act as both an input and at least one mode of output for kiosk 10.

As further shown in FIG. 1, kiosk 10 can include a stand 26 onto which test seat 12 and control units 22a and 22b are mounted. As shown, test seat 12 can be mounted to stand 26 by way of one or more tracks 28, which allow test seat 12 to slide in a fore and aft direction with respect to stand 26. In this manner, test seat 12 can move toward and away from one or more features, such as foot ramp 30, which can replicate the position of a similar feature within a vehicle (such as vehicle 110 in FIG. 7). In the illustrated embodiment, foot ramp 30 can replicate the general position and shape of features within adjacent foot well of a vehicle, which can include positions for the gas pedal, brake pedal, and other features therein. By allowing test seat 12 to be positioned with respect to, for example, foot ramp 30, the position of an occupant within vehicle 110 can be more closely replicated, thereby potentially allowing more accurate measurements via kiosk 10. Other similar features can be included in kiosk 10, including various surfaces replicating positions of arm rests, consoles, a vehicle steering wheel, or dashboard.

Figure 2:
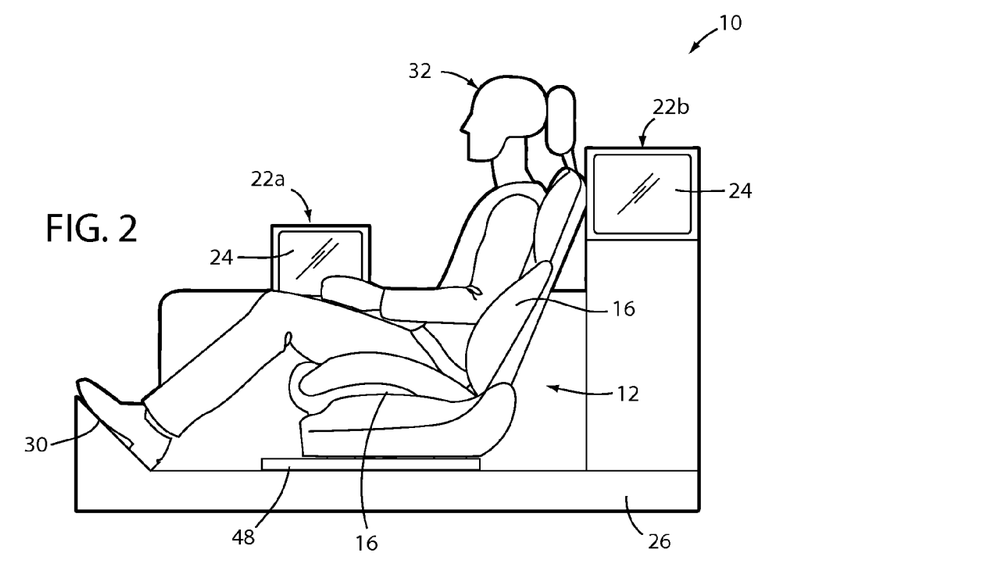
FIG. 2 is a side elevational view of the kiosk of FIG. 1 with an occupant positioned on a test seat thereof.

As shown in FIG. 2, kiosk 10 is configured such that an occupant 32 can position herself or himself on test seat 12 within kiosk 10 in a seated position that generally replicates the position of the occupant 32 in a similar vehicle seat 112 within a vehicle 110. When occupant 32 is in position on test seat 12, kiosk 10 can be directed, either by occupant 32 or a designated operator, to carry out a measurement procedure, examples of which are discussed further below. As discussed above, sensors 18 can be coupled with electronic circuitry within kiosk 10, such as a computer, microprocessor, or the like that can receive force measurements from sensors 18 relating to localized forces on seating surface 20 by occupant 32. The electronic circuitry can be programmed to associate the force measurements received from the various ones of sensors 18 with the particular locations thereof along seating surface 20. In an example, the particular locations of the various sensors 18 can be pre-programmed into the electronic circuitry. In this manner, sensors 18 can be used by kiosk 10 to determine a weight distribution profile for occupant 32 along seating surface 20. This can include various comparisons of the sensed forces in the designated areas thereof, such as by determining an average force among sensors 18 and identifying particular areas that deviate by a predetermined amount from such average. In other instances, absolute forces obtained by sensors 18 can be compared against a baseline. Further, forces between adjacent ones of sensors can be interpolated from available data to provide an approximate weight distribution profile along the entirety of seating surface 20.

Figure 3:
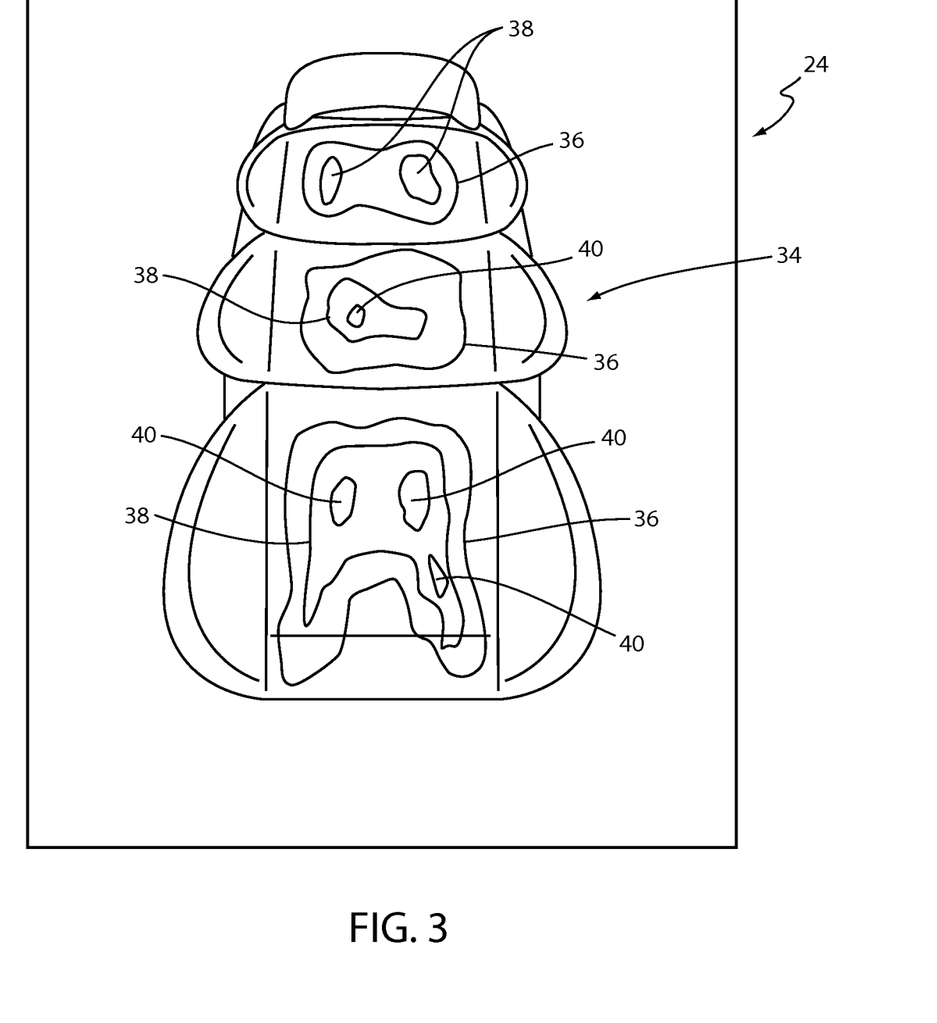
FIG. 3 is a representation of an image presentable on a display associated with the kiosk.

As shown in FIG. 3, one possible output mode for kiosk 10 is to generate a graphical representation of the determined weight distribution for occupant 32 and to output the graphical representation on one or more displays 24 included in kiosk 10. Such an output can include a seat image 34 that may generally replicate test seat 12 or may depict test seat 12 schematically. A contact map 36 showing the locations within which occupant 32 makes contact with seating surface 20, or areas where the force applied by occupant 32 on seating surface 20 exceeds a predetermined threshold, can be displayed in an overlaid manner with respect to seat image 34. As depicted, contact maps 36 can be depicted as contour maps, showing various areas 38 within contact maps 36 that are greater than the determined average force of weight distribution by a predetermined amount (e.g. about 10% or greater) with additional areas being identified as localized pressure points 40, which further exceed the baseline or average weight distribution force by a greater amount than areas 38 (e.g. about 20% or greater) such image 34 can be made available to occupant 32 and/or an operator of kiosk 10 to help in manually deriving a custom configuration for a related vehicle seat or for information purposes to convey the need for such a customized seat arrangement, which may be generated by kiosk 10 according to various modes described below.

Kiosk 10, as depicted in FIGS. 1 and 2, can further include data storage such as internal memory or the like (not shown), which can be used to store the seat image 34 and/or related weight distribution data for occupant 32, in a manner such that the particular occupant 32 for which the data is derived can also be stored and associated with occupant 32. Additionally, kiosk 10 can include a wired or wireless data output, such as a universal serial bus ("USB") port and/or a wireless internet communication device (such as Wi-Fi, Bluetooth, or the like) such that the weight distribution data, seat image 34, and parameters related to custom seat configuration (described further below) can be outputted from kiosk 10 to a remote device or location. In one example, kiosk 10 can be capable of uploading such data to cloud-based storage for use in factory-customization of a vehicle seat based on the data obtained by kiosk 10 and/or loading of such custom seat parameters into memory of a selected vehicle such that a determined seat configuration can be implemented by a seat control system of that particular vehicle. In other examples, the data from kiosk 10 relating to such seat configurations can be downloaded by occupant 32 or an operator to a USB drive, portable computer, tablet, or the like for loading into a particular vehicle or transmission to a factory, dealer service center, or the like.

As mentioned previously, the electronic circuitry within kiosk 10 can be programmed to provide any number of customized seat configurations for a vehicle seat 112 that corresponds generally to test seat 12. In one example the corresponding vehicle seat 112 can have a number of portions thereof that are configured to be moveable with respect to each and to otherwise alter the shape of seating surface 120 and/or the various firmnesses and hardnesses of individual portions thereof. In one example, a vehicle seat 112 can have moveable portions corresponding to the lumbar area 142, as well as cervical seat area 144, central cushion area 146, and thigh extension area 148. Additionally, the entirety of back 116 can be moveable with respect to cushion 114. Test seat 12 can itself include areas that correspond in shape to such areas of vehicle seat 112, such areas being optionally moveable in the same manner as in vehicle seat 112. Accordingly, a custom seat arrangement derived by kiosk 10 using the force measurements from test seat 12 can correspond to a configuration for vehicle seat 112. Such a configuration can be such that the various moveable parts of vehicle seat 112 are positioned relative to each other according to a determination made in response to the forces measured by sensors 18 in test seat 12. Measurement of such forces by test seat 12 can be obtained with test seat 12 fixed in a predetermined test arrangement or by movement of test seat 12 through a predetermined test sequence, kiosk 10 being configured to monitor the various positions and configurations of such moveable or configurable portions thereof. Further, a derived custom seat arrangement can be confirmed by appropriate movement of test seat 12 into such an arrangement.

Figure 7:
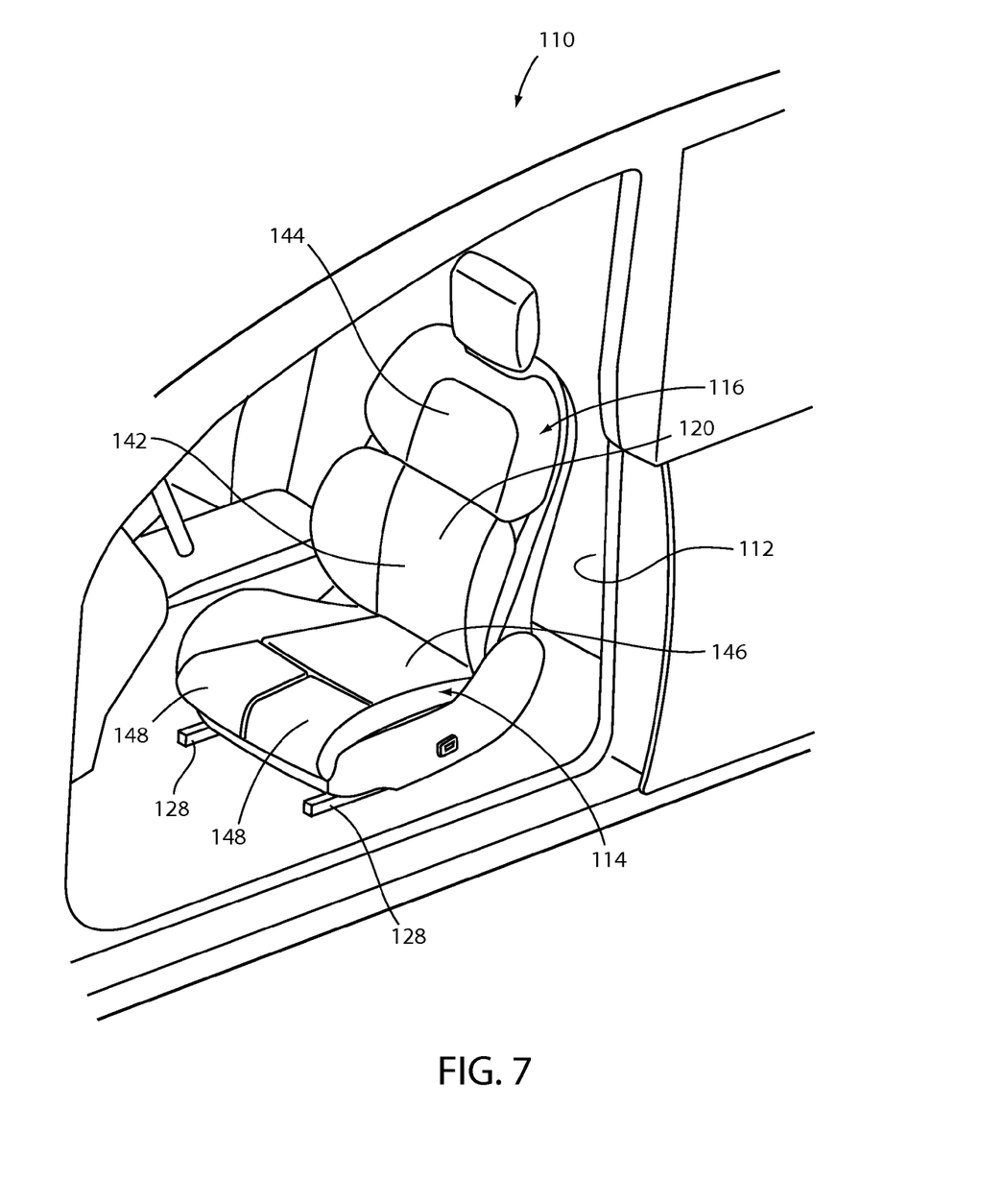
FIG. 7 is a partial view of a vehicle interior including a seat that may be customized according to the method of FIGS. 4-6 or using the kiosk of FIG. 1.

Although the vehicle seat 112 shown in FIG. 7 has the general appearance of a front vehicle seat and is illustrated in the position of a driver's seat, kiosk 10, or variations thereof according to the general principles described herein, can be used to provide customized configurations for passenger seats, including both front and rear passenger seats (both bucket-style or bench-style). For customization of such seats, corresponding variations of kiosk 10 can be provided to replicate such seats, or kiosk 10 can be programmed to limit the test adjustment of test seat 12 or the output thereof to correspond to available adjustments of particular seats. Still further, variations of the kiosk 10 shown herein can be implemented to provide similar custom configurations for office chairs and other articles of furniture.

In an example, if a pressure point 40 is detected toward the aft section of cushion 14, but detected pressures toward the forward portion of cushion 14 at or near the baseline pressure, the electronic circuitry of kiosk 10 can determine that cushion 114 of vehicle seat 112 can be adjusted in an angle such that the rearward portion thereof is lowered relative to the front portion thereof to more evenly distribute the weight of the occupant along cushion 114 so as to compensate for variations of the weight distribution over test seat 12, at least in the initial configuration thereof, thereby reducing the sensed force or forces in one or more identified problem areas. Similarly, if uneven pressure is detected along back 16, such as between lumbar area 42 and cervical area 44, the corresponding portions of vehicle seat 112 can be directed to move in a manner so as to balance out such forces. In further examples, vehicle seat 112 corresponding to test seat 12 may include one or more inflatable bladders within, for example lumbar area 142 and cushion 114. Accordingly, a custom seat configuration derived from kiosk 10 can adjust the absolute and relative inflation levels among the various bladders to achieve a desired pressure profile.

In one embodiment, test seat 12 can be such that the various portions thereof, which correspond to moveable, or configurable, portions of vehicle seat 112 are also moveable through a predetermined range of motion and/or inflation in test seat 12. This can include movement of various portions, such as cushion 14, and back 16 relative to each other, for example, as well as having one or more inflatable bladders (not shown) positioned within test seat 12 and in fluid communication with a pump or other inflation device or unit (not shown) within kiosk 10. In such an embodiment, kiosk 10 can cause test seat 12 to run a test sequence, wherein solutions are tested by positioning test seat 12 within a determined custom configuration, while obtaining data from sensors 18 regarding the weight distribution of occupant 32 in such configurations, as well as data related to the positions or inflation levels of the various moveable and/or configurable portions of test seat 12. Using data, received thusly, a custom configuration can be determined, or further refinement can be performed. Additionally or alternatively, vehicle seat 112 can have portions thereof wherein the seat cushioning foam or underlying suspension elements included in the construction of vehicle seat 112 can be removed and substituted with either softer or firmer replacement cushions or suspension element (such as with softer or firmer springs or the like). In such an example, the electronic circuitry within kiosk 10 can determine areas of vehicle seat 112 where such different cushioning or suspension elements may be desired and can direct an operator of kiosk 10 to facilitate such replacement, which can be done, for example, by a dealer, or a factory during assembly during a custom-ordered vehicle.

Figure 4:
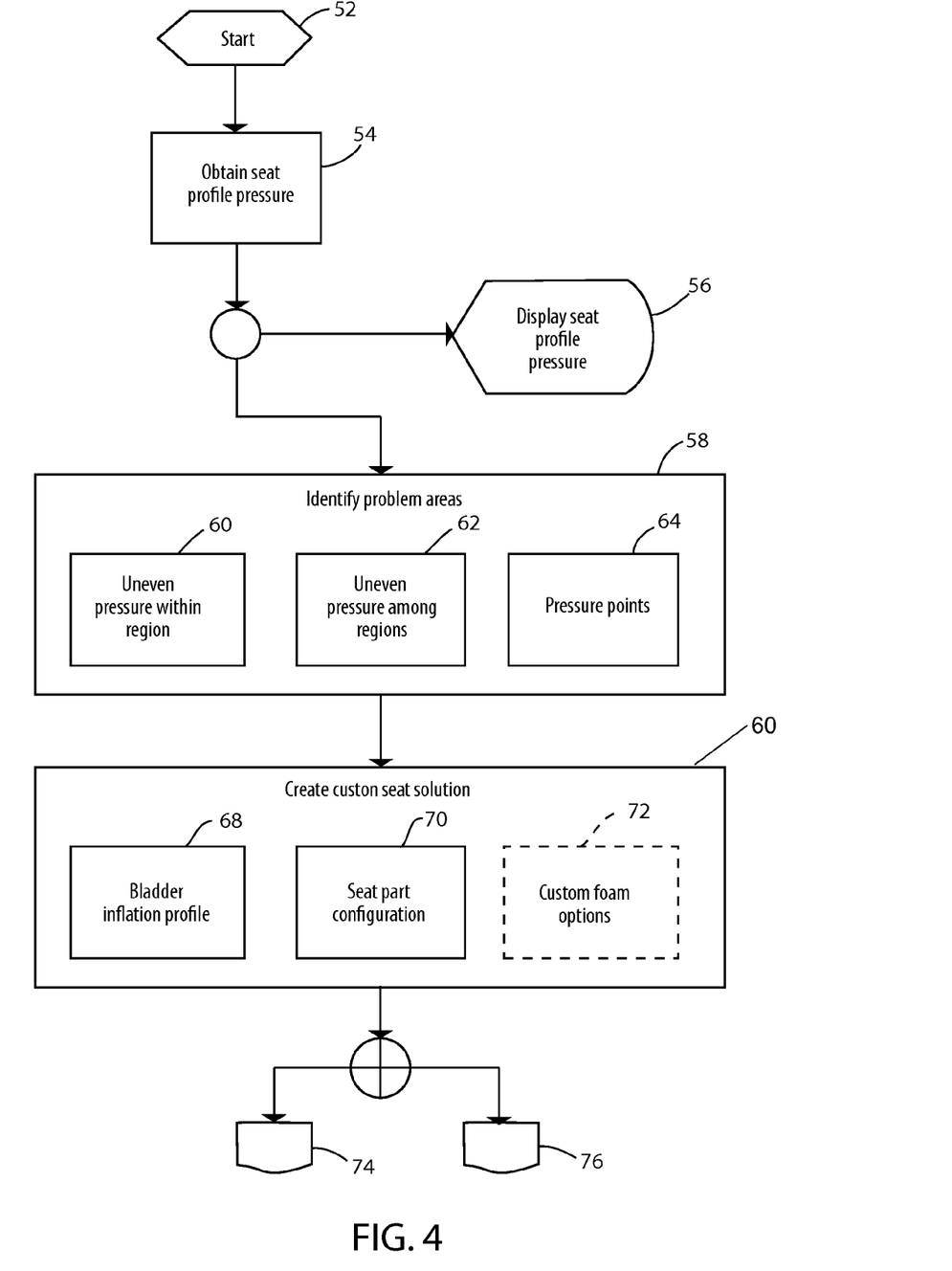
FIG. 4 is a flow chart showing a portion of a method for customizing a vehicle seat that may be implemented by the kiosk of FIG. 1.
Figure 5:
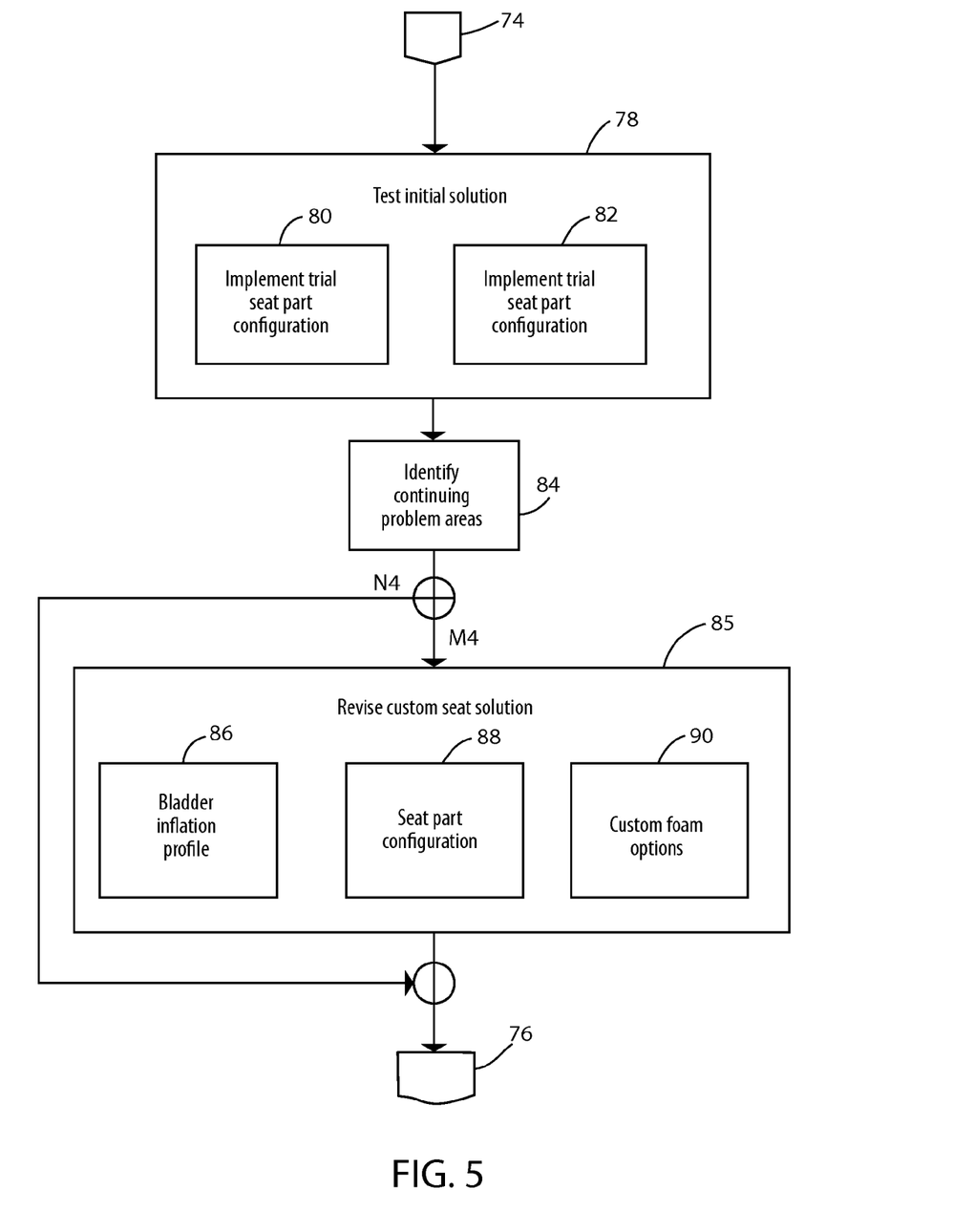
FIG. 5 is a flow chart showing an additional portion of the method for customizing a vehicle seat.
Figure 6:
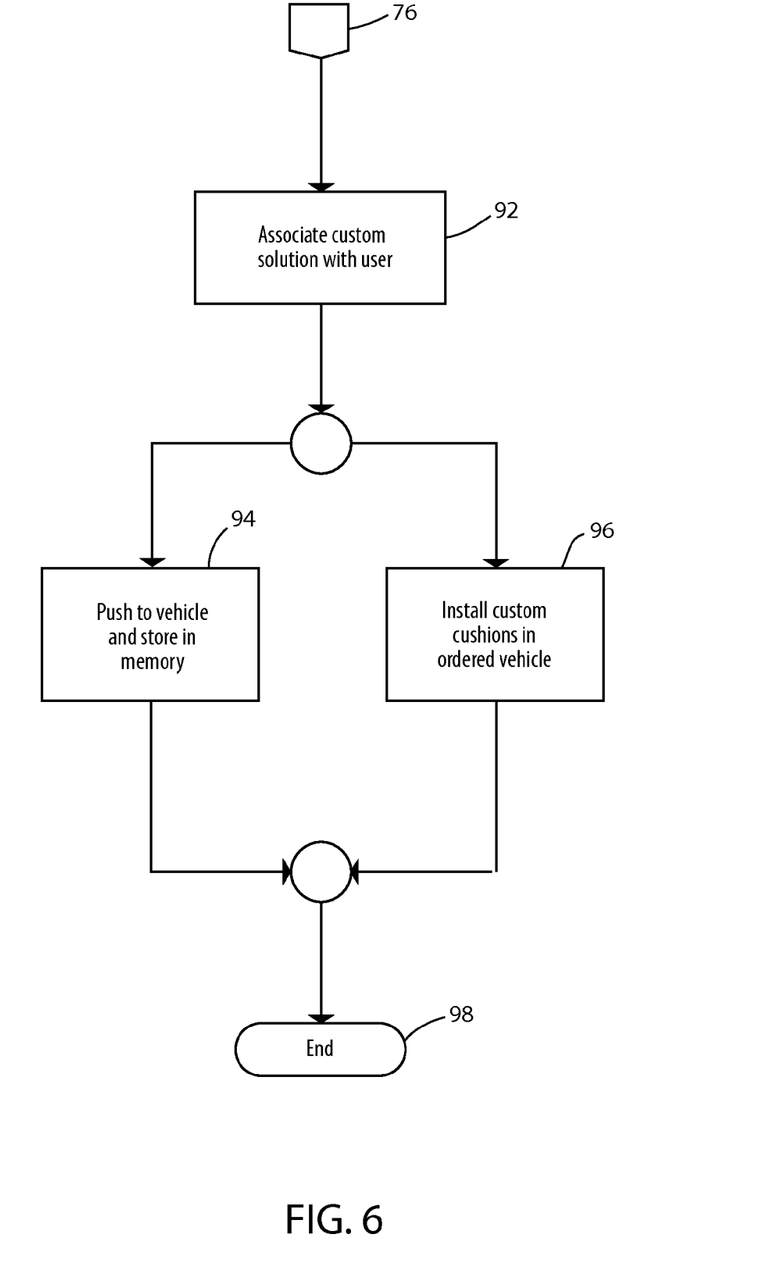
FIG. 6 is a flow chart showing an additional portion of the method for customizing a vehicle seat.

Various steps in a method for obtaining a custom vehicle seat arrangement using kiosk 10, as described above, are discussed herein with reference to FIGS. 4-6. Such a method can be carried out automatically by kiosk 10, such as in response to initiation by an occupant 32 of test seat 12 using control unit 22a, or at the direction of an operator using control unit 22b. Additionally, certain steps may be carried out manually by a specifically-trained operator using information outputted by kiosk 10 on display 24. As shown in FIG. 4, the method can be started in step 52, which can include positioning occupant 32 on test seat 12 and entering an appropriate command on control unit 22a or 22b to begin the measurement process. Subsequently, kiosk 10 can obtain data in the form of force measurements and associate the force measurements with location information of the sensors 18 to derive a seat pressure profile, as discussed above with respect to FIGS. 2 and 3, in step 54. As further discussed above with respect to FIG. 3, kiosk 10 can display the seat pressure profile, such as by of image 34 on display 24, which can optionally be done in step 56. The pressure profile obtained can then be analyzed, such as by comparison to a baseline force among the particular areas of sensors 18, or by comparison against an average of all forces obtained by sensors 18 in comparison with the particular forces among the sensed areas. Such analysis can identify potentially problematic areas along seating surface 20 in step 58. As discussed above, such problem areas can include areas such as elevated pressure areas 38 that reflect an uneven pressure in a lateral direction across the seating surface 20 within a particular region, such as along cushion 14 (step 60). Such problem areas can also include an area of test seat 12, such as lumbar area 42 having a greater pressure than an adjacent region such as a cervical seat area 44 (step 62), or pressure points 40, as discussed above (step 64).

Subsequently, in step 66 the method can include the creation of a custom seat solution, which can include the development of a bladder inflation profile (step 68), or the positioning of the various moveable parts of the vehicle seat 112, as discussed above, (step 70). As also discussed above, such a seat configuration can optionally include the selection of various replacement foam inserts with different hardnesses, which may correspond to various areas of the vehicle seat 112.

As discussed above, test seat 12 may be configured to test the solution developed in step 66, in which case the method can continue, in step 74, to a testing sequence in step 78 (FIG. 5). In testing the initial seat configuration solution, test seat 12 can be reconfigured, including by movement of cushion 14, seat back 16, as well as lumbar area 42, cervical area 44, and thigh extension 48 in step 80. Additionally, test seat 12 can implement a trial bladder configuration in step 82 wherein various bladders including throughout test seat 12 can be inflated to levels determined by kiosk 10. Subsequently kiosk 10 can take additional measurements from force sensors 18, including obtaining a revised seat pressure profile in step 84 to determine if any problem areas still exist. If such areas do exist, the seat solution can be revised in a manner similar to which it was initially derived including adjusting the bladder inflation profile in step 86, revising the seat part configuration (step 88), and recommending custom foam options in step 90. In an example, when a test sequence is included in the method, the initial custom seat solution (step 66) may not include custom foam options in step 72, but may, instead provide custom foam options in step 90 as part of a revised custom seat solution when problem areas persist, despite the derived bladder inflation profile and seat part configuration.

After a test sequence, or in a method where a test sequence is not used, the method can proceed to step 76, wherein kiosk 10 can associate the derived custom seat solution with the occupant 32 for which it is derived, such as by entering the name of occupant 32 using control unit 22a or 22b and/or entering a customer's vehicle order number or the vehicle identification number of the occupant's vehicle. Subsequently, kiosk 10 can push the custom solution to a vehicle 110 associated with occupant 32, where it is stored in memory within the vehicle 110 to be implemented in vehicle seat 112 (step 94). Additionally or alternatively kiosk 10 can output information regarding particular custom cushions for vehicle seat 112 which can be ordered, for example by a dealer, or specifically installed with a new vehicle ordered by occupant 32 (step 96). Other output options for kiosk 10 are available, as discussed above, and include the use of a USB drive or a memory card for importing into vehicle 110 of occupant 32, or generating a particular code corresponding to a custom seat solution that can be implemented by vehicle 110, or the like. Subsequently, the method can end in step 98.

In another embodiment, a vehicle seat, such as vehicle seat 112 in FIG. 7 can include a plurality of sensors, similar to sensors 18 in FIG. 1. Such sensors can be electrically coupled with an on-board computer system of vehicle 110. In such an example, the on-board computer of vehicle 110 can be programmed to obtain a weight distribution profile of an occupant of vehicle seat 112 in a manner similar to that carried out using test seat 12 of kiosk 10. Using such data, vehicle 110 can itself develop a custom configuration for vehicle seat 112 in a manner similar to that which is performed by the electronic circuitry of kiosk 10 discussed above.

It will be understood by one having ordinary skill in the art that construction of the described invention and other components is not limited to any specific material. Other exemplary embodiments of the invention disclosed herein may be formed from a wide variety of materials, unless described otherwise herein.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the invention as shown in the exemplary embodiments is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present invention. The exemplary structures and processes disclosed herein are for illustrative purposes and are not to be construed as limiting.

What is claimed is:
1. An apparatus for customizing a vehicle seat, comprising:
   a stand;
   a test vehicle seat on the stand having a cushion and a back coupled thereto, the test vehicle seat matching a surface contour and an adjustment mode set of the vehicle seat;
   a plurality of force sensors in respective locations along the cushion and the back;
   electronic circuitry coupled with the plurality of sensors and programmed to output a vehicle seat configuration compensating for forces sensed by ones of the plurality of force sensors within corresponding locations of the vehicle seat, the vehicle seat lacking such force sensors, wherein the electronic circuitry is programmed to output the sensed forces and associated areas as an image of the test seat with the sensed forces depicted within the image so as to correspond to the respective locations of the sensors;
   a first video screen mounted on the stand in a position facing the test vehicle seat; and
   a second video screen mounted on the stand in a position facing away from the test vehicle seat, the image being output to at least one of the first video screen and the second video screen and displayed thereon.

2. The apparatus of claim 1, wherein:
the adjustment mode set of the vehicle seat includes a plurality of adjustable pneumatic bladders at various locations; and
the test vehicle seat is a modified vehicle seat having the plurality of force sensors isolated in locations corresponding to the locations of the pneumatic bladders.

3. The apparatus of claim 1, further including a control coupled with the electronic circuitry, the electronic circuitry further programmed to receive input from the control and to implement a measurement process in response thereto, the measurement process including:
the associating of the forces sensed by respective ones of the plurality of force sensors with the particular locations thereof along the cushion and the back;
deriving the vehicle seat configuration according to the forces and the associated areas; and
the output of the derived vehicle seat configuration.

4. The apparatus of claim 1, further including memory coupled with the electronic circuitry, wherein the electronic circuitry is further programmed such that output of the sensed forces and associated areas as data is output at least to the memory.

5. The apparatus of claim 1, further including an internet communication device coupled with the electronic circuitry, wherein the electronic circuitry is further programmed such that the output of the derived vehicle seat configuration is output at least to a remote device using the internet communication device.

6. The apparatus of claim 1, wherein:
the cushion is moveable with respect to the back, the test seat further including a motor for moving the cushion with respect to the back and coupled with the electronic circuitry; and
the electronic circuitry is further programmed to implement a test sequence including movement of the back with respect to the cushion.

7. The apparatus of claim 6, wherein:
the adjustment mode set of the vehicle seat includes a plurality of adjustable pneumatic bladders at various locations; and
the electronic circuitry is further programmed to associate the forces sensed by respective ones of the plurality of force sensors with inflation levels of the bladders and a position of the back with respect to the cushion and to output the associated inflation levels and positions.

8. A method for customizing a vehicle seat, comprising:
obtaining data related to a weight distribution of an occupant over a test seat in a test configuration and including a cushion, a back, and a plurality of force sensors distributed along the cushion and the back, the data being obtained using the sensors;
determining a custom configuration for a vehicle seat having a surface contour and an adjustment mode set matched by the test seat, the custom configuration being based on the weight distribution data of the occupant;
outputting the configuration to a vehicle including the vehicle seat; and
automatically adjusting the vehicle seat into the configuration.

9. The method of claim 8, wherein determining the custom configuration is carried out to compensate for variations in the weight distribution over the test seat.

10. The method of claim 8, wherein:
the step of obtaining data includes obtaining force measurements from the plurality of force sensors and associating the force measurements with particular locations thereof along the cushion and the back; and
the step of determining the custom configuration includes determining an average force of the force measurements and identifying ones of the particular locations wherein one of the force measurements associated therewith is greater than the average force by at least about 10 percent.

11. The method of claim 10, wherein the step of determining the custom configuration further includes:
identifying a configurable portion of the vehicle seat that includes one of the identified ones of the particular locations; and
providing an output including configuration data for the configurable portion determined to be capable of reducing the one of the force measurements associated therewith.

12. The method of claim 11, wherein the configuration data includes one of:
position information for the configurable portion within a range of motion thereof;
inflation level information for the configurable portion within a range of inflation thereof; and
information relating to a selected hardness of the configurable portion.

13. The method of claim 8, wherein the test seat has a plurality of force sensors in locations corresponding to pneumatic bladder locations in the vehicle seat.

14. The method of claim 8, wherein:
the data obtained using the force sensors includes sensed forces;
the step of obtaining data further includes implementing a test sequence including:
executing a program including instructions to move the cushion of the test seat with respect to the back; and
associating the sensed forces with a position of the back with respect to the cushion.

15. The method of claim 8, further including executing a program to display a seat image with the force measurements depicted in locations along the image that correspond to the locations of the sensors.

16. A kiosk for providing a custom configuration for a vehicle seat, comprising:
a stand;
a test seat on the stand, the test vehicle seat matching a surface contour and an adjustment mode set of the vehicle seat and having a plurality of force sensors distributed adjacent a seating surface thereof;
electronic circuitry coupled with the plurality of sensors;
a control coupled with the electronic circuitry and operable to instruct the electronic circuitry to obtain force measurements from the sensors and to output a vehicle seat configuration compensating for the force measurements within corresponding locations of the vehicle seat, the vehicle seat lacking force sensors, and an image of the test seat with the sensed forces depicted within the image so as to correspond to the respective locations of the sensors;
a first display mounted on the stand in a position facing the test seat and coupled with the electronic circuitry, the electronic circuitry operable to output information related to the might measurements thereon; and
a second video screen mounted on the stand in a position facing away from the test vehicle seat, the image being output to at least one of the first video screen and the second video screen and displayed thereon.

17. The kiosk of claim 16, wherein the control is programmed to:
- obtain data related to a weight distribution for an occupant using the force sensors; and
- determine the custom configuration for a seat based on the weight distribution data for the occupant.

18. The kiosk of claim 17, wherein:
- the test seat includes a cushion and a back rotatably coupled with the cushion, the seating surface extending over the cushion and the back, and the plurality of force sensors being further distributed among the cushion and the back; and
- the control is programmed to;
    - obtain the weight distribution data by obtaining force measurements from the plurality of force sensors and associating the force measurements with particular locations thereof along the cushion and the back; and
    - to determine the custom configuration by determining an average of the force measurements and identifying ones of the particular locations wherein a particular one of the force measurements associated therewith is greater than the average of the force measurements by at least about 10 percent.

\* \* \* \* \*

UNITED STATES PATENT AND TRADEMARK OFFICE
CERTIFICATE OF CORRECTION

| | | |
|---|---|---|
| PATENT NO. | : 9,771,003 B2 | Page 1 of 1 |
| APPLICATION NO. | : 14/526591 | |
| DATED | : September 26, 2017 | |
| INVENTOR(S) | : Kolich et al. | |

It is certified that error appears in the above-identified patent and that said Letters Patent is hereby corrected as shown below:

In the Claims

Column 10:
Claim 16, Line 63;
"might" should be --force--.

Column 11:
Claim 18, Line 13;
";" should be --:--.

Signed and Sealed this
Nineteenth Day of December, 2017

Joseph Matal
*Performing the Functions and Duties of the*
*Under Secretary of Commerce for Intellectual Property and*
*Director of the United States Patent and Trademark Office*